United States Patent [19]
Chartrain et al.

[11] Patent Number: 5,958,743
[45] Date of Patent: Sep. 28, 1999

[54] STEREOSPECIFIC BIOCONVERSION OF BENZYL ACETOACETATE TO BENZYL-(S)-(+)-HYDROXYBUTYRATE

[75] Inventors: Michel Chartrain, Westfield; James M. McNamara, Rahway, both of N.J.

[73] Assignee: Merck & Co., Inc., Rahway, N.J.

[21] Appl. No.: 08/803,852

[22] Filed: Feb. 28, 1997

Related U.S. Application Data

[60] Provisional application No. 60/012,692, Mar. 1, 1996.
[51] Int. Cl.$^6$ .................. C12P 7/00; C12P 7/62; C12P 41/00
[52] U.S. Cl. ............... 435/135; 435/132; 435/254.22; 435/255.4; 435/280; 435/921
[58] Field of Search ............... 435/132, 135, 435/280, 921, 254.22, 255.4

[56] References Cited

U.S. PATENT DOCUMENTS

| | | | |
|---|---|---|---|
| 4,933,282 | 6/1990 | Hasegawa et al. | 435/135 |
| 5,508,461 | 4/1996 | Ito et al. | 558/58 |
| 5,567,314 | 10/1996 | Chigusa et al. | 435/921 |

*Primary Examiner*—Herbert J. Lilling
*Attorney, Agent, or Firm*—Michael D. Yablonsky; Jack L. Tribble

[57] ABSTRACT

A bioconversion process where benzyl acetoacetate is converted to benzyl-(S)-(+)-3-hydroxybutyrate.

1 Claim, No Drawings

STEREOSPECIFIC BIOCONVERSION OF BENZYL ACETOACETATE TO BENZYL-(S)-(+)-HYDROXYBUTYRATE

CROSS-REFERENCE TO RELATED APPLICATIONS

This application claims the benefit of U.S. Provisional Application Ser. No. 60/012,692, filed Mar. 1, 1996.

STATEMENT REGARDING FEDERALLY-SPONSORED R&D

Not applicable.

REFERENCE TO MICROFICHE APPENDIX

Not applicable.

FIELD OF THE INVENTION

Fermentation and biotransformation.

BACKGROUND OF THE INVENTION

A bioconversion process employing *Candida schatavii* strain MY 1831 is presented. In this bioconversion process benzyl cetoacetate is converted to benzyl-(S)-(+)-3-hydroxybutyrate.

SUMMARY OF THE INVENTION

A bioconversion process employing *Candida schatavii* strain MY 1831 is presented. In this bioconversion process benzyl acetoacetate is converted to benzyl-(S)-(+)-3-hydroxybutyrate.

BRIEF DESCRIPTION OF THE DRAWINGS

Not applicable.

DETAILED DESCRIPTION OF THE INVENTION

A bioconversion process employing *Candida schatavii* strain MY 1831 is presented. In this bioconversion process benzyl acetoacetate is converted to benzyl-(S)-(+)-3-hydroxybutyrate.

The present invention is directed to a fermentation process which employs a readily prepared culture medium. Culture medium as used herein is defined as a mixture which supports the growth of yeast cells, which mixture contains ingredients such as peptone, soy peptone, and yeast extract powder. It should be understood that the precise amounts of ingredients provided above may be optimized, or modified so long as no new components are introduced. The key aspect of the medium is its ability to support growth of *Candida schatavii* and thereby the production of benzyl-(S)-(+)-3-hydroxybutyrate by bioreduction of benzyl acetoacetate.

In general, the product compounds may be produced by culturing (fermenting) the above-described microorganism in the presence of an appropriate amount of benzyl acetoacetate substrate in an aqueous nutrient medium containing sources of assimilable carbon and nitrogen, preferably under submerged aerobic conditions (e.g. shaking culture, submerged culture, etc.). The aqueous medium is incubated at a temperature between 26° C. and 29° C., preferably 28° C. The aqueous medium is incubated for a period of time necessary to complete the biotransformation as monitored by HPLC, usually for a period of about 24–48 hours, on a rotary shaker operating at about 220 rpm with a throw of about 2 in.

Submerged aerobic cultural conditions may be preferred for the production of product compounds in massive amounts. For the production in small amounts, a shaking or surface culture in a flask or bottle is employed.

Accordingly, it is desirable first to produce a vegetative inoculum of the organism by inoculating a relatively small quantity of culture medium with cells produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of product compounds and is generally autoclaved to sterilize the medium prior to inoculation.

Agitation and aeration of the culture mixture may be accomplished in a variety of ways. Agitation may be provided by a propeller or similar mechanical agitation equipment, by revolving or shaking the fermentation flask, by various pumping equipment or by the passage of sterile air through the medium. Aeration may be effected by passing sterile air through the fermentation mixture.

The fermentation is usually conducted at a temperature between 20° C. and 35° C., for a period of about 24 hours to 48 hours, which may be varied according to fermentation conditions and scales. Preferably, the production cultures are incubated for about 48 hours at 28° C. on a rotary shaker operating at 220 rpm.

Preferred culturing/production media for carrying out the fermentation include the Sabouraud Dextrose medium (30 g/L; Difco).

The biotransformation product may be recovered from the culture medium by conventional means which are commonly used for the recovery of other known biologically active substances. The product compounds are found filtrate, which are obtained by filtering or centrifuging the cultured broth, and accordingly can be isolated and purified by a conventional method such as concentration under reduced pressure, lyophilization, extraction with a conventional solvent, such as ethylacetate and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using ethylacetate.

The compounds of the present invention have the following structures. Compound (I), benzyl acetoacetate is the starting material. Compound (II) is the product, benzyl-(S)-(+)-3-hydroxybutyrate.

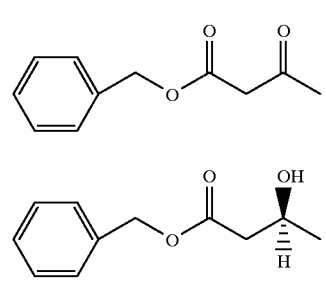

A sample of *Candida schatavii* was deposited under the Budapest Treaty in the American Type Culture Collection, 12301 Parklawn Drive, Rockville, Md. 20852, USA on Apr. 9, 1998 and has been assigned accession number 74439.

EXAMPLE 1

Preparation of Substrate

The substrate, benzyl acetoacetate may be prepared via a synthetic process or may be purchased commercially.

EXAMPLE 2

Preparation of Benzyl-(S)-(+)-3-Hydroxybutyrate

A chemical reference for desired product was prepared as follows. Methyl (S)-(+)-3-hydroxybutyrate (Aldrich) was dissolved in benzyl alcohol and treated with a catalytic amount of titanium tetraisopropoxide. The mixture was aged at 60° C. for 24 hours. Partial concentration on a rotary evaporator and filtration afforded benzyl (S)-(+)-3-hydroxybutyrate and residual benzyl alcohol.

EXAMPLE 3

Analytical Procedures

An amount of 5 ul of the extract resuspended in methylene chloride was spoted on a TLC plate (Kiesel precoated silica gel 60, F254), and was developed in a chromatography chamber using a mixture of hexane/ethyl acetate (5/1). Starting materials (benzyl acetocete) and product (benzyl-(S)-(+)-3-hydroxybutyrate) were observed under ultraviolet light. An authentic racemic sample of benzyl-3-hydroxybutyrate was used for reference purposes. Chirality of the produced benzyl-(S)-(+)-3-hydroxybutyrate was determined by high pressure liquid chromatography (HPLC). The enantiomers were separated using a Chiralcel OD column (Chiral Technologies), employing a mobile phase comprised of a mixture of 98% hexane and 2% isopropanol at a flow rate of 0.6 ml/min.

EXAMPLE 4

Shake Flask Fermentations

Yeast cells were preserved on slants of Sabouraud dextrose agar (Difco) kept at 4° C. Cells were obtained from the slants using a sterile loop and used to inoculate a 250-ml Erlenmeyer flask containing 50-ml of Sabouraud dextrose broth. The cultures were incubated aerobically at 28° C. for 48 hours on a shaker operated at 220 rpm. A volume of 2.5 ml of this 48 h-old culture was used to inoculate a 250-ml Erlenmeyer flask containing 50 ml of Sabouraud dextrose medium. The cultures were incubated in the same conditions as described above for 24 hours. After 24 hours of incubation, the substrate for bioconversion (benzyl acetoacetate) was added to each flask in 1 ml of ethanol to give a final concentration of 1 g/l. The cultures were incubated for 24 hours under the same conditions.

After that 24-hour incubation, the whole content of the flasks were harvested. A volume of 50 ml of ethyl acetate was added to each broth, and the mixtures were shaken for 10 minutes, followed by a 10 minute centrifugation at 2500 rpm in a bench top centrifuge. The ethyl acetate layer was separated from the water layer and taken to dryness. After TLC and HPLC analyses, *Candida schatavii* strain MY 1831 was found to produce benzyl-(S)-(+)-3-hydroxybutyrate with an enantiomeric excess of 93%.

EXAMPLE 5

NMR Analyses

Identification of the benzyl-(S)-(+)-3-hydroxybutyrate was done by proton NMR. Proton NMR spectra were recorded with $CD_3OD$ (49.1 ppm) as internal standard. The resonance of the benzyl-(S)-(+)-3-hydroxybutyrate are: 1.24 ppm (3H, d), 2.52 ppm (2H, m), 4.23 ppm (1H, m), 5.18 ppm (2H, s), 7.37 ppm (5H, s).

What is claimed:

1. A method of converting benzyl acetoacetate to benzyl-(S)-(+)-3-hydroxybutyrate comprising:

(a) cultivating *Candida schatavii* strain MY 1831 ATCC 74439 in a medium containing benzyl acetoacetate; and (b) recovering the benzyl-(S)-(+)-3-hydroxybutyrate.

* * * * *